United States Patent [19]

Taylor et al.

[11] Patent Number: 5,019,652
[45] Date of Patent: May 28, 1991

[54] CATALYSTS AND METHOD

[75] Inventors: Charles E. Taylor; Richard P. Noceti, both of Pittsburgh, Pa.

[73] Assignee: The United States as represented by the United States Department of Energy, Washington, D.C.

[21] Appl. No.: 516,611

[22] Filed: Apr. 30, 1990

[51] Int. Cl.$^5$ ............................................. C07C 51/215
[52] U.S. Cl. ..................................... 562/549; 562/609; 570/244; 502/227; 502/229
[58] Field of Search ................ 562/541, 549; 570/243, 570/244; 585/642; 502/229, 227

[56] References Cited

U.S. PATENT DOCUMENTS

| | | | |
|---|---|---|---|
| 3,420,901 | 1/1969 | Schulz | 570/243 |
| 4,123,389 | 10/1978 | Pieters et al. | 252/441 |
| 4,194,990 | 3/1980 | Pieters et al. | 252/441 |
| 4,665,270 | 5/1987 | Brophy et al. | 585/642 |
| 4,769,504 | 9/1988 | Noceti et al. | 585/415 |

OTHER PUBLICATIONS

PCT/GB84/00429 International Application, June 20, 1985.
European Patent Application No. 0117731 to Bromhead.
Louderback, "Formic Acid and Derivatives", Kirk-Othmer Encyclopedia of Chemical Technlogy, Second Edition, vol. 10, pp. 99–113.
Applied Catalysts, 11 (1984), pp. 35–71.
Taylor and Noceti, "Novel Catalysts for the activation of Methane", Poster Session, May 7, 1989, American Catalysis Society, Dearborn, MI.

Primary Examiner—Patrick P. Garvin
Assistant Examiner—Brent M. Peebles
Attorney, Agent, or Firm—Hugh W. Glenn; Robert J. Fisher; William R. Moser

[57] ABSTRACT

An improved catlayst and method for the oxyhydrochlorination of methane is disclosed. The catalyst includes a pyrogenic porous support on which is layered as active material, cobalt chloride in major proportion, and minor proportions of an alkali metal chloride and of a rare earth chloride. On contact of the catalyst with a gas flow of methane, HCl and oxygen, more than 60% of the methane is converted and of that converted more than 40% occurs as monochloromethane. Advantageously, the monochloromethane can be used to produce gasoline boiling range hydrocarbons with the recycle of HCl for further reaction. This catalyst is also of value for the production of formic acid as are analogous catalysts with lead, silver or nickel chlorides substituted for the cobalt chloride.

10 Claims, 8 Drawing Sheets

CATALYSTS AND METHOD

CONTRACTUAL ORIGIN OF THE INVENTION

The U.S. Government has rights in this invention pursuant to the employee/employer relationship of the inventor to the U.S. Department of Energy at the Pittsburgh Energy Technology Center.

BACKGROUND OF THE INVENTION

The present invention relates generally to catalysts and methods for converting light hydrocarbons into monohaloalkanes and other useful products. In particular, the invention is directed to the production of monochloromethane and formic acid from methane. As has been described in the inventors' prior U.S. Pat. No. 4,769,504, entitled "Process for Converting Light Alkanes to Higher Hydrocarbons", issued Sept. 6, 1988, monochloromethane so produced can be further processed to form gasoline boiling range hydrocarbons. This prior U.S. patent is hereby incorporated by reference for describing this process.

The need to supplement petroleum supplies has stimulated research and the production of chemicals and fuels from other sources. Methane from natural gas and from the conversion of coal is a source of considerable interest for such production.

It is well known that methane can be converted to methanol by reformation with steam and that the methanol thus produced can be further processed over a crystalline aluminosilicate catalyst to form gasoline boiling range hydrocarbons. Such a process is described in U.S. Pat. No. 3,928,483 to Chang et al.

Monohalomethanes can be prepared as disclosed in European Patent Application No. 0117731 and as suggested in PCT Publication No. W085102608, converted to higher hydrocarbons over crystalline aluminosilicates. It has long been thought that the monohalides are much preferred in such processes with only low levels of polyhalogenated alkanes tolerated for effective conversion. Such monohalomethanes can be produced by reaction of chlorine or other halogens with methane which requires elevated temperatures above 450° C. or by the oxyhalogenation of methane using a suitable catalyst such as the halide salts of copper, nickel, iron or palladium. Such procedures as are described in the above cited European Patent Application are characterized by low conversions, generally less than about 35%.

An oxyhydrochlorination catalyst containing copper chloride, potassium chloride and a rare earth chloride is disclosed in U.S. Pat. No. 4,123,389 to Pieters et al. This catalyst is reported to provide substantially higher values of methane conversion, but to result in substantial polychlorination. Previously, this catalyst was of particular interest in the production of carbon tetrachloride as a feed stock for chlorofluorocarbon-refrigerants.

This invention also relates to the production of formic acid as a co-product to monohalide alkanes. Typically, formic acid is produced by the reaction of sulfuric acid with sodium formate in the presence of 85-90% formic acid. Adequate cooling of the reaction mixture and the presence of the added formic acid as a reaction medium limits decomposition of the product. Sodium formate is formed by the reaction of sodium hydroxide and carbon monoxide, such as from producer gas that is carefully cleaned and compressed to 12-18 atmospheres. The sodium formate crystals are obtained by drying the reaction product prior to reaction with the sulfuric acid.

The major commercial use of formic acid is in the textile and leather industries as an effective disinfectant and preservative. It acts as a dye exhausting agent for various fabrics and for other functions in dying and treating textiles. Formic acid serves as an intermediate in the preparation of various esters and amides. Methyl and ethyl formate have value as solvents, fumigants and pesticides. Formamide is of particular interest as it has considerable value in the manufacture of pharmaceuticals, agricultural chemicals and dyes.

SUMMARY OF THE INVENTION

Therefore, in view of the above, it is an object of the present invention to provide a process for the coproduction of monohalomethanes and formic acid.

It is also an object of the invention to provide a method for the production of monochloromethane with recoverable concentrations of formic acid.

It is a further object of the invention to provide a catalyst for the production of monochloromethane with limited production of polychloromethanes.

It is likewise an object of the invention to provide a two-stage conversion process of methane to gasoline range hydrocarbons with a co-product of formic acid.

It is a further object of the invention to provide oxyhydrochlorination catalysts for the co-production of monochloromethane and formic acid.

It is also an object of the invention to provide an improved oxyhydrochlorination catalyst for the conversion of methane to monochloroalkanes with enhanced methane conversion and reduced production of polychloromethanes.

In accordance with the present invention, a catalytic method for the production of monochloromethane with recoverable concentrations of formic acid in aqueous solution with limited polychloromethane production includes providing an oxyhydrochlorination catalyst with a pyrogenic support material carrying a first layer of catalyst including a metal chloride deposited on the support. The metal chloride selected is from the group of chlorides including cobalt, lead, nickel and silver. A second catalyst layer includes alkali metal chlorides and permissibly a rare earth chloride deposited on the support. The catalyst is contacted with a reactant gas mixture containing methane, HCl and oxygen at reactant conditions to produce a normalized carbon-product distribution of at least 20 mol % formic acid and with monochloromethane in excess of the total polychloromethane production.

In other aspects of the invention, the formic acid is separated from other carbon products by condensation in a formic acid-water solution and concentrated to a constant boiling composition of formic acid and water. Concentrations in the range of 75-90% formic acid are obtained by fractional distillation, azeotropic distillation and solvent extraction.

In one other aspect of the invention, the gas mixture contacts a catalyst at a temperature of about 300° C. to 450° C. for a residence time of about 7-10 seconds.

After separating the monochloromethane from aqueous formic acid, it can be dried and reacted over a crystalline aluminosilicate catalyst to produce hydrocarbons in the C5 to C10 gasoline boiling point range. HCl produced in the second reaction can be recycled to the oxyhydrochlorination catalysts for further production of monochloromethane.

The invention also comprehends an oxyhydrochlorination catalyst for the co-production of monochloromethane and formic acid from methane. The catalyst in major proportion is a metal chloride selected from the chlorides of cobalt, nickel, lead and silver along with a minor proportion of alkali metal chlorides permissibly including a rare earth chloride. The active catalyst materials are supported on a pyrogenic carrier selected from silica titania and alpha alumina. Preferably, the catalyst employs cobaltous chloride in about 40–60 weight % along with 10–20 weight % of a mixture of potassium chloride and lanthanum chloride supported on a silica carrier at about 20–40 % by weight.

DETAILED DESCRIPTION OF THE DRAWINGS

The present invention is illustrated in the accompanying drawings wherein.

DETAILED DESCRIPTION OF THE INVENTION

Figure 1:
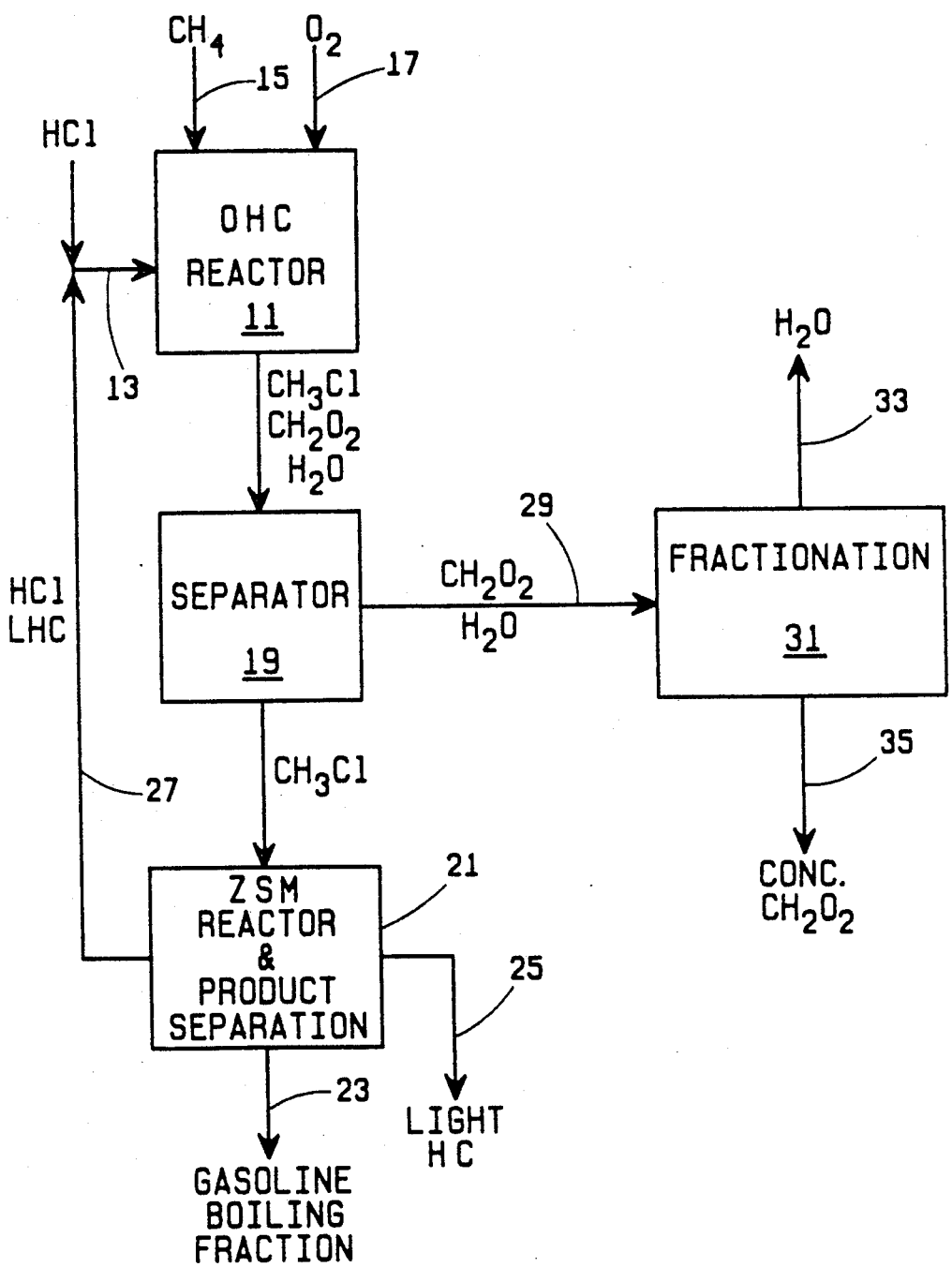
FIG. 1 is a flow diagram of a hydrocarbon reforming process in which methane is converted to monochloromethane, formic acid and higher hydrocarbons.
Figure 2:
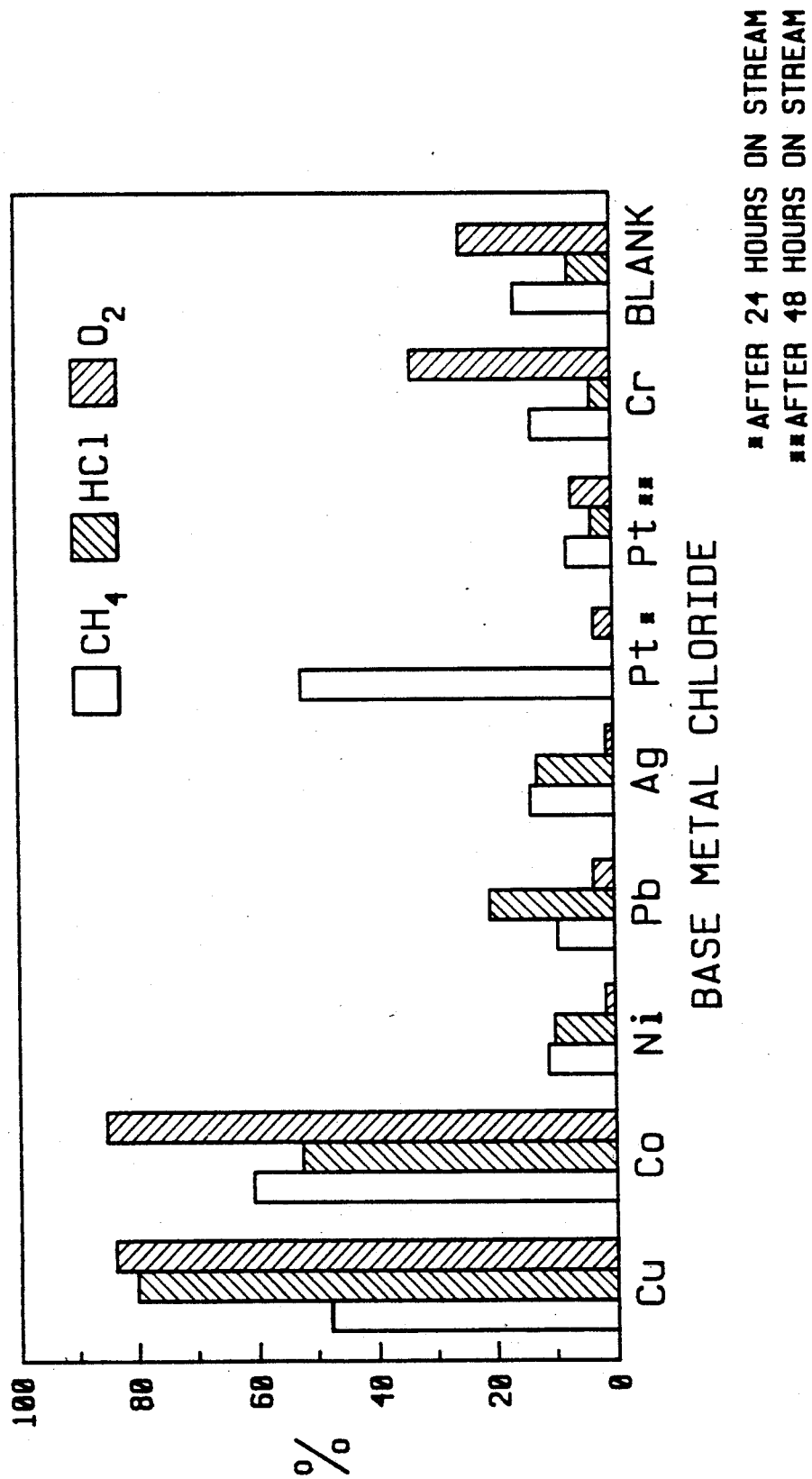
FIG. 2 is a bar chart illustrating reactant conversion for various catalysts.
Figure 3:
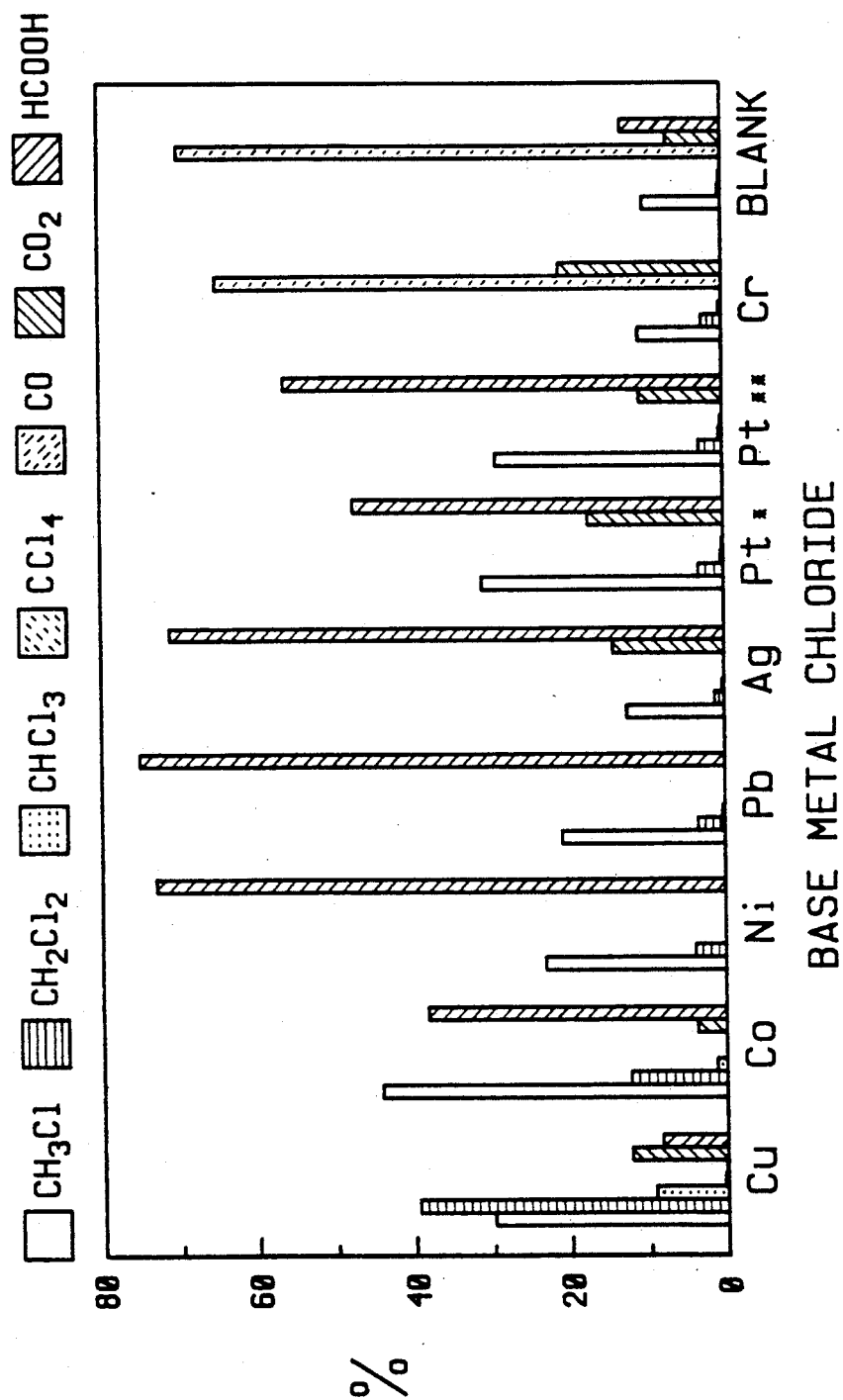
FIG. 3 is a normalized product distribution for the oxyhydrochlorination reaction with various catalysts.
Figure 4:
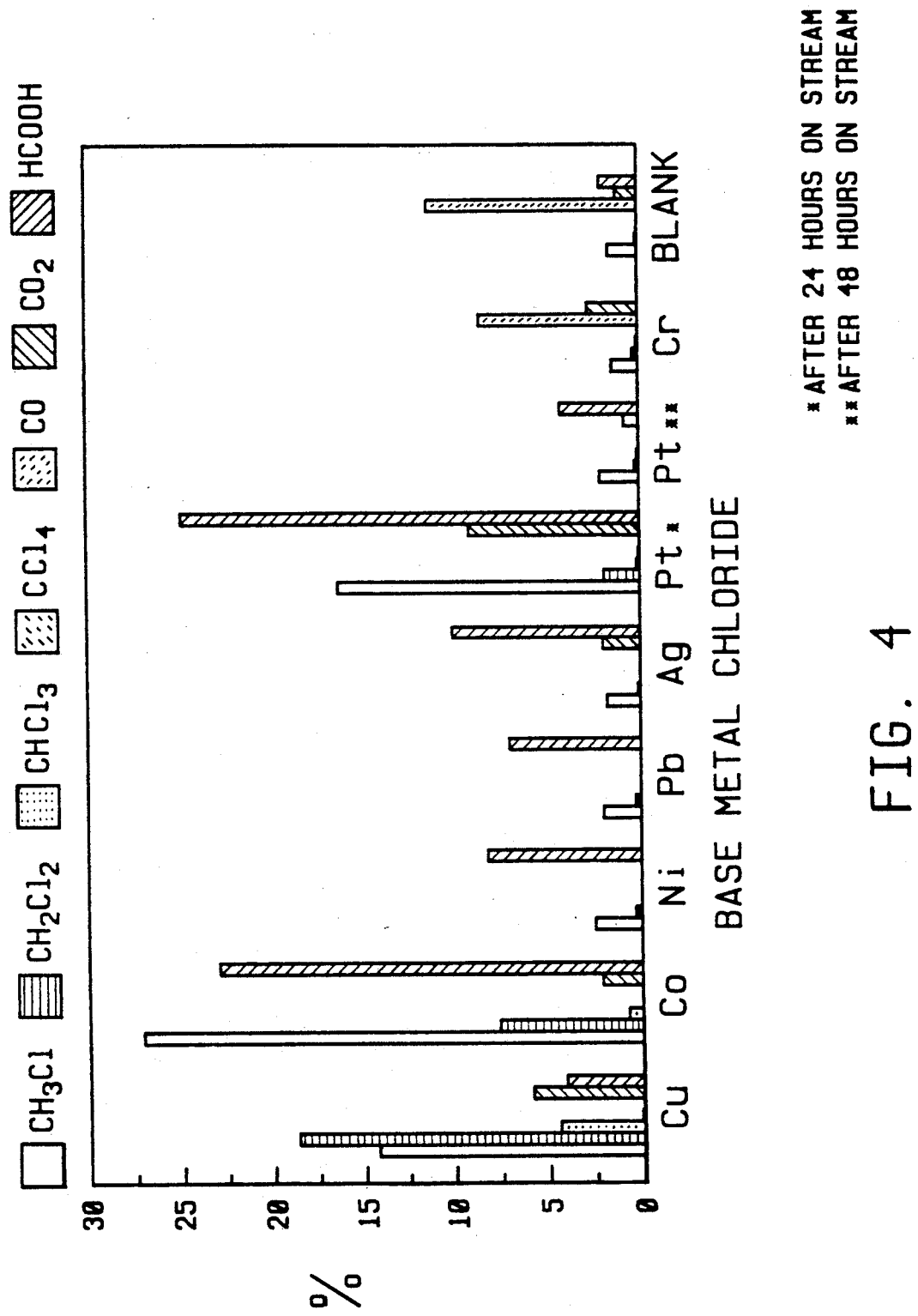
FIG. 4 is a bar chart showing the reaction product distribution expressed as methane conversion times normalized product distribution for the various catalysts.

Referring now to FIG. 1 wherein oxyhydrochlorination reactor 11 is provided with a feed of HCl 13, methane 15 and oxygen 17 for reaction over an oxyhydrochlorination catalyst. The catalyst is selected particularly for the co-production of monochloromethane and formic acid with limited production of polychloromethanes such as dichloromethane, trichloromethane and carbon tetrachloride. The inventors have found that the chlorides of cobalt, nickel, lead and silver are particularly advantageous for this purpose. Preferably, for the balanced production of monochloromethane and formic acid, cobaltous chloride is selected as the catalyst. The active metal chloride is supported on a pyrogenic oxide such as silica, titania or alpha alumina as a first layer and is coated with a second layer of an alkali metal chloride such as potassium chloride and permissively a minor proportion of the rare earth chloride. The resulting product containing monochloromethane, formic acid and water in principal amounts along with minor amounts of dichloromethane, trichloromethane and carbon dioxide is passed into a separator 19 wherein the formic acid and water is condensed from the monochloromethane and other carbon containing products.

As is described in the above cited U.S. Pat. No. 4,769,504, the monochloromethane is thoroughly dried and passed on to a second reactor 21 containing a zeolite catalyst for producing gasoline boiling range fraction products 23 (within the C-5 and C-10 range) and light hydrocarbons 25 (C-3 and C-5 range). HCl released in this reaction is separated and recycled to the oxyhydrochlorination reactor 11 for reaction with additional methane and oxygen. Permissibly, the light hydrocarbons or a portion thereof, also may be recycled to the oxyhydrochlorination reactor for further processing.

It is advantageous to include minor proportions of polychloromethanes or other polychloroalkanes to be condensed over the zeolite catalysts as they may promote formation of aromatic and branched-chain hydrocarbons in the product. However, the inventors have found that polychloroalkanes approaching the concentration of the monochloromethane can have a deleterious effect on the zeolite catalyst. This has been a disadvantage of the copper based oxyhydrochlorination catalysts as they tend to produce polychlorinated alkanes up to and in excess of the monochloromethane product. Accordingly, it is preferred that the normalized product distribution based on carbon include monochloromethane in excess of the total molar concentration of the more highly chlorinated hydrocarbons.

Water and formic acid separated from the chlorinated hydrocarbons at 29 are passed on to a fractionation process 31 in which water 33 is separated from the more highly concentrated formic acid product 35. Typically, formic acid concentration of 20–30% in water can be separated by condensation from the reaction products produced with a cobalt chloride catalyst. In contrast, the condensation product corresponding to flow 29 in a process using a copper-based oxyhydrochlorination catalyst will include economically unrecoverable concentrations of formic acid of only about 0.5–2%. With the copper catalyst not only is less formic acid produced, but also a greater proportion of water is produced in the reactions leading to the polychloroalkanes.

The following four reactions show the conversion of methane to monochloromethane, dichloromethane, trichloromethane and to formic acid. It is seen that the production of the polychloromethanes adds increasing amounts of water into the product stream that must subsequently be removed.

| METHANE CONVERSION REACTIONS |
| --- |
| $CH_4 + HCl + \frac{1}{2} O_2 \rightarrow CH_3Cl + H_2O$ |
| $CH_4 + 2HCl + O_2 \rightarrow CH_2Cl_2 + 2H_2O$ |
| $CH_4 + 3HCl + 3/2 O_2 \rightarrow CHCl_3 + 3H_2O$ |
| $CH_4 + 3/2 O_2 \rightarrow CH_2O_2 + H_2O$ |

Advantageously, nickel, lead and silver catalysts provide even higher concentrations of formic acid typically in excess of 40 mol %.

These aqueous solutions of formic acid can be readily concentrated to constant boiling mixtures of formic acid containing between 75 and 85% acid depending on the pressure of fractionation. Azeotropic distillation with propyl formate gives a non-aqueous phase which can be further distilled to yield anhydrous formic acid. The separated aqueous phase typically will contain less than about 1% formic acid. Such methods for separating formic acid are described in Louderback, *Formic Acid and Derivatives,* KIRK-OTHMER ENCYCLOPEDIA OF CHEMICAL TECHNOLOGY, 2nd ED., Vol. 10, pages 99–113.

The following examples are presented merely by way of illustration and are not intended to limit the invention beyond that defined in the claims.

EXAMPLE I

An oxyhydrochlorination catalyst containing cobalt chloride was prepared by thoroughly dissolving cobaltous chloride, $CoCl_2$ in acetonitrile, $CH_3CN$. Particulate silicon dioxide (Cab-O-Sil® HS-5) was added to the solution with swirling followed by standing overnight to thoroughly impregnate the cobaltous chloride into the silicon dioxide support. The acetonitrile was then slowly evaporated under aspiration with slow rotation over a period of about four hours. The temperature was increased slowly to 60° C. and then held to prevent any rapid boiling that could interfere with the uniform distribution of the catalyst into the support. The resulting blue solid was then slowly dried under vacuum overnight at a temperature of 90°-110° C. Potassium chloride (KCl) and lanthanum chloride ($LaCl_3$) were dissolved in 98% formic acid and this solution was added to the cobaltous chloride-silica powder and allowed to stand overnight. The formic acid was then evaporated under aspiration with rotation until a tacky solid was formed. The rotation was stopped and the temperature slowly increased to 60° C. and held until all of the formic acid was removed. The resulting blue solid was dried overnight under vacuum at a temperature of 90° to 110° C. The blue powder as thus formed included a first layer of crystalline cobaltous chloride uniformly distributed on the silica support with a second layer of potassium chloride and lanthanum chloride deposited over the cobaltous chloride.

Scanning Electron Photomicrography has shown that the catalysts in their most active forms have crystalline materials on their surfaces and that catalysts of the same chemical composition with lesser activities have less crystalline materials on their surfaces. It has been found that the surface topography of these catalysts, and thus their activities, is directly related to the method of preparation. In order to make the more active catalysts with highly crystalline surfaces, great care must be taken during the evaporation of the various solvents when layering the supports with the metal chlorides. High solvent evaporation rates and rapid tumbling during evaporation lead to materials with lower surface crystallinity and lower catalytic activity.

EXAMPLE II

A lead oxyhydrochlorination catalyst was prepared in much the same way Example I except lead acetate ($Pb(OAc)_2$) was dissolved in methanol to be deposited onto the silica support. After drying the resulting white solid it was exposed to gaseous hydrochloric acid (HCl) for sufficient time to convert the lead acetate to lead chloride ($PbCl_2$). A second catalytic layer of potassium chloride and lanthanum chloride was then deposited in much the same manner as described in Example I.

Various other oxychlorination catalysts in accordance with the present invention as well as copper chloride and blank catalysts were prepared for comparison in a manner similar to that described in Examples I and II. The catalysts compositions are given below in Table I.

TABLE I

| | CONSTITUENTS BY WEIGHT | | | |
|---|---|---|---|---|
| CATALYST | % METAL CHLORIDE | % $SiO_2$ | % KCl | % $LaCl_3$ |
| Cu | 41.66 | 37.50 | 11.46 | 9.38 |
| Co | 55.17 | 28.82 | 8.81 | 7.20 |
| Ni | 58.46 | 26.70 | 8.16 | 6.68 |
| Pb | 66.96 | 21.24 | 6.49 | 5.31 |
| Ag | 44.73 | 35.53 | 10.86 | 8.88 |
| Pt | 41.66 | 37.50 | 11.46 | 9.38 |
| Cr | 56.24 | 28.12 | 8.61 | 7.03 |
| BLANK | 0.00 | 64.29 | 19.64 | 16.07 |

EXAMPLE III

An oxyhydrochlorination catalyst as described in Example I with cobaltous chloride in an amount of about 3 grams was exposed to equal flows of methane and HCl (4.0 milliliters/minute) and about one half that flow (2.0 milliliters/minute) of oxygen diluted with 2 milliliters per minute of nitrogen at about 340° C. and a residence time of 8.3 seconds. The flow was continued for over 48 hours resulting in a methane conversion of about 61%, HCl conversion of about 53% and an oxygen conversion of about 85%.

Similar runs made with various other catalysts were conducted and the reactant conversions given below in Table II.

TABLE II

| | REACTANT CONVERSION | | |
|---|---|---|---|
| CATALYST | % $CH_4$ CONV | % HCl CONV | % $O_2$ CONV |
| Cu | 47.69 | 80.08 | 83.86 |
| Co | 61.03 | 52.54 | 85.48 |
| Ni | 19.31 | 19.81 | 11.11 |
| Pb | 5.51 | 14.86 | 9.41 |
| Ag | 4.54 | 7.95 | 14.03 |
| Pt[a] | 54.34 | 0.01 | 3.10 |
| Pt[b] | 7.36 | 3.29 | 6.56 |
| Cr | 13.15 | 3.54 | 33.21 |
| BLANK | 16.16 | 6.63 | 25.31 |

Figure 5:
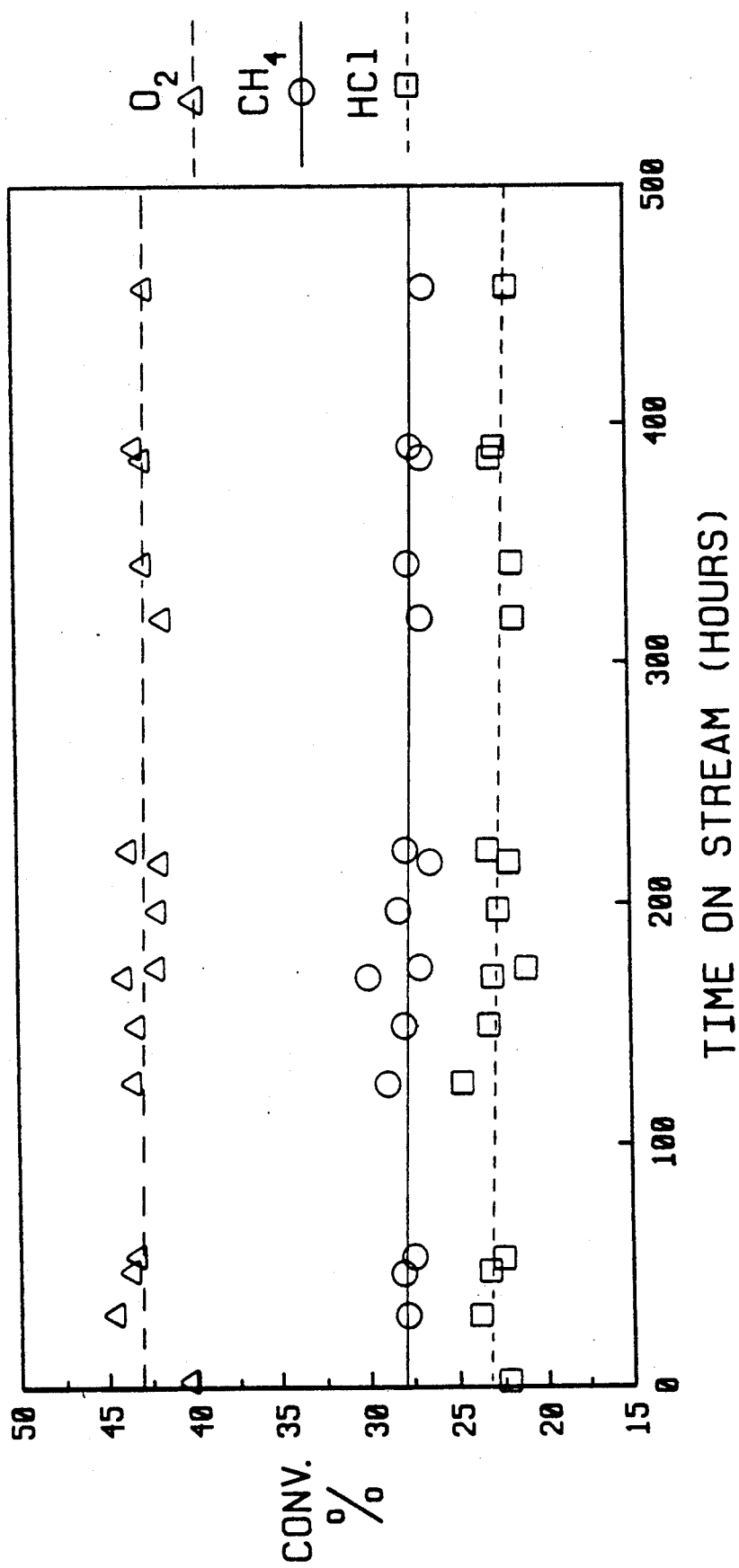
FIG. 5 is a graph showing reactant conversion as a function of time for the cobalt catalyst.
Figure 6:
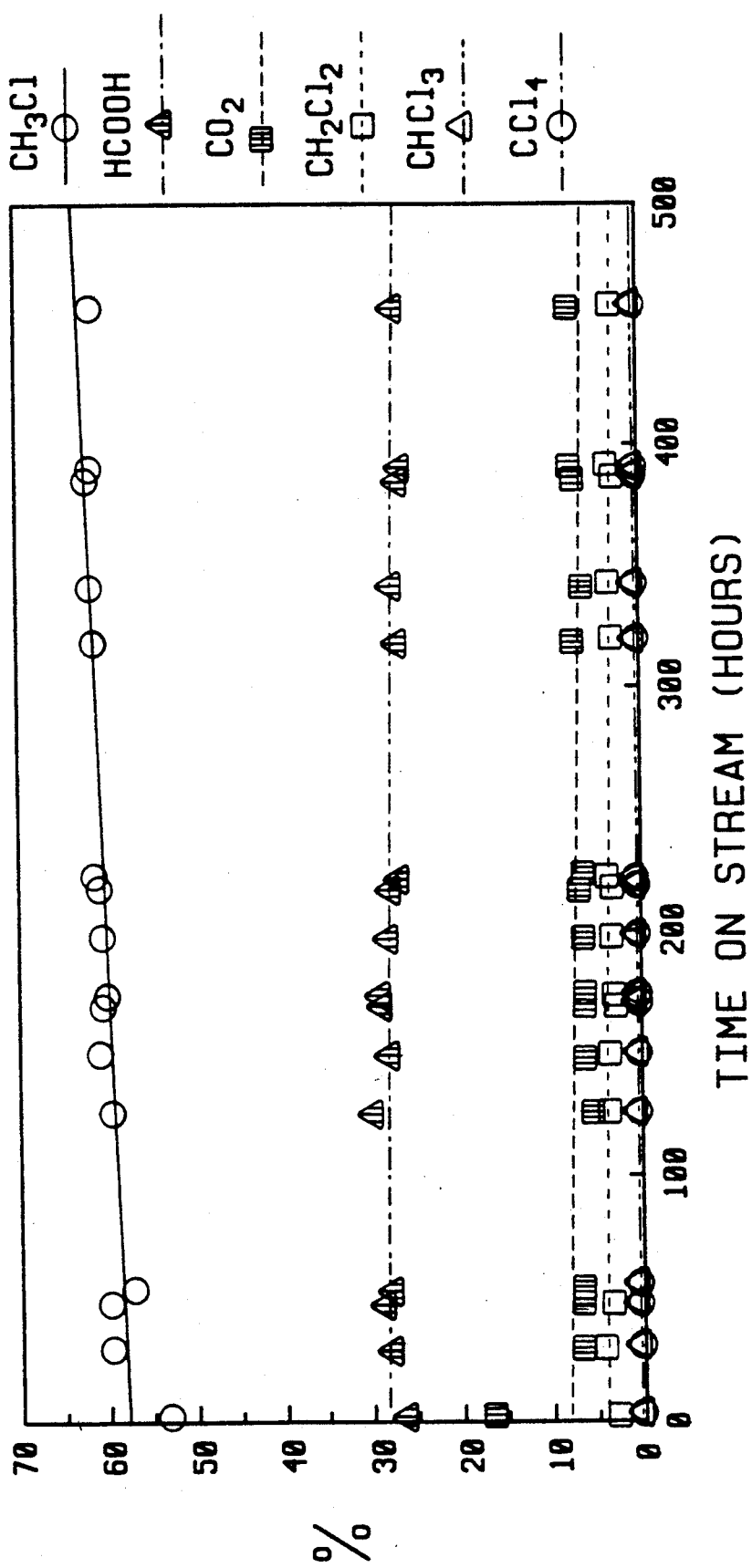
FIG. 6 is a graph showing normalized product distribution as a function of time for the cobalt catalyst.

Each of the catalysts, other than platinum, maintained nearly constant conversion over the full period. The platinum catalyst was found to degrade substantially after 48 hours of reaction. Subsequent tests with the other catalysts conducted for over 400 hours showed the cobalt, nickel, lead and silver catalysts to be stable over the full time period. FIG. 5 illustrates the constant conversion rates for the cobaltous chloride catalyst. The lower conversion percentages are attributed to a more rapid stripping of the acetonitrile than that described in Example I resulting in less crystalline $CoCl_2$ deposited.

Unexpectedly, the cobalt chloride catalyst was found to have higher selectivity for monochloromethane in preference to polychloromethanes of any of the catalysts tested. In addition, this catalyst produced substantial amounts of formic acid within the aqueous phase.

Figure 7:
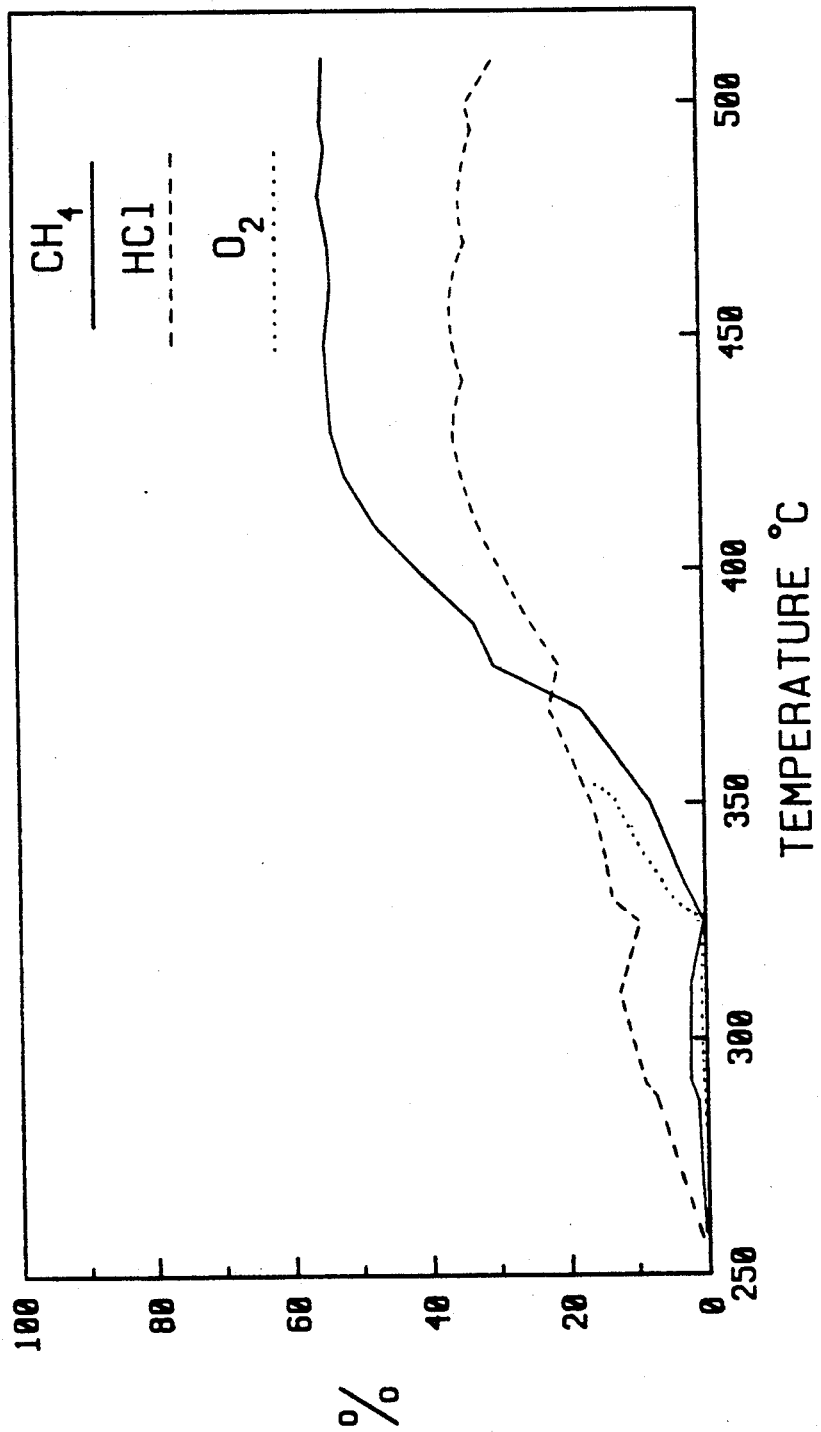
FIG. 7 is a graph showing reactant conversion as a function of temperature for the lead catalyst.
Figure 8:
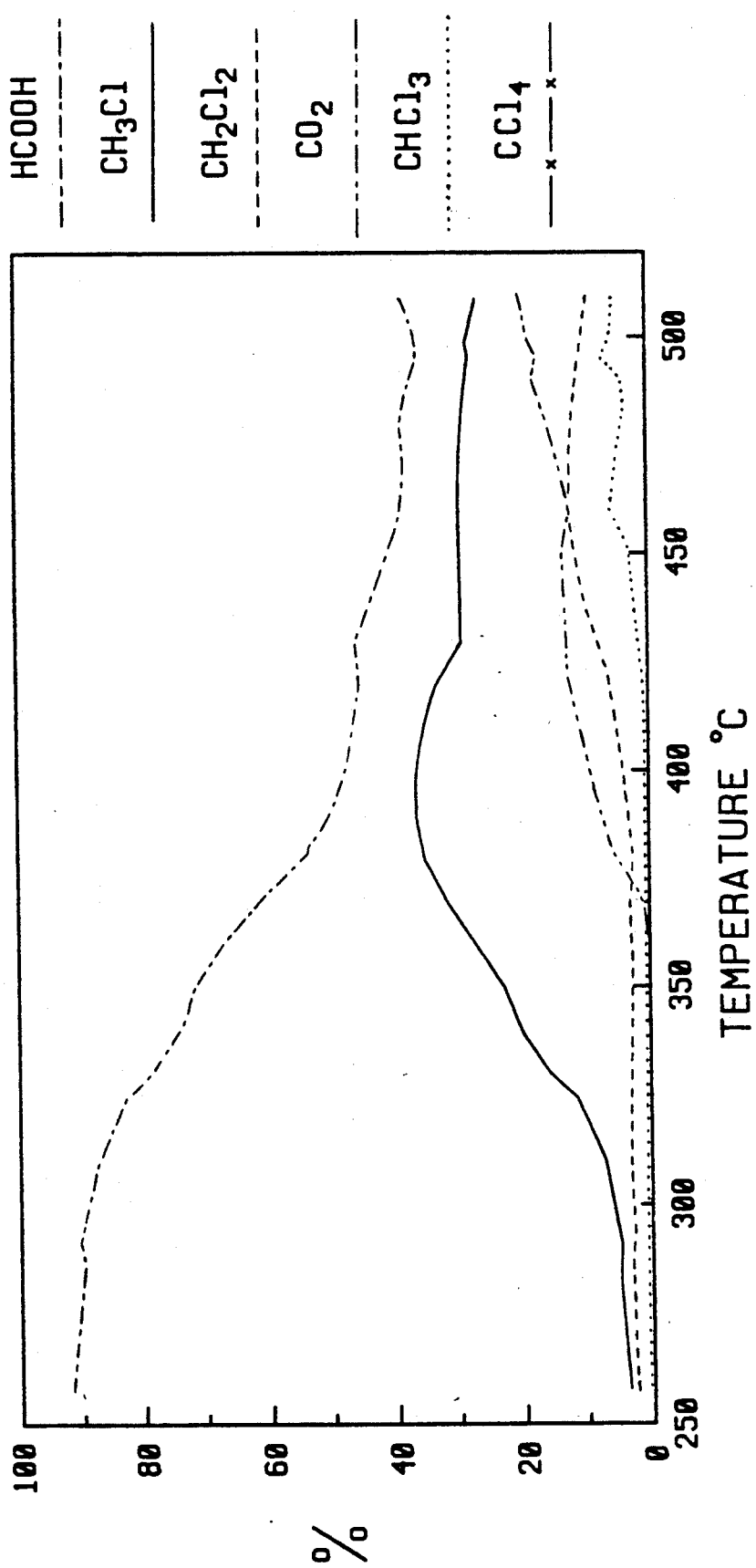
FIG. 8 is a graph showing normalized product distribution as a function of temperature for the lead catalyst.

Nickel, lead and silver catalysts also produced advantageous results with high selectivity for formic acid and good selectivity of monochlormethane over the polychloromethanes. The performance of the $PbCl_2$ catalyst is illustrated in FIGS. 7 and 8 where increased conversion of methane with good selectivity for monochloromethane is obtain at temperatures of 350°-450° C.

The results of the normalized carbon distribution of he various catalysts are listed below in Table III.

TABLE III

| CATALYST | NORMALIZED CARBON PRODUCT DISTRIBUTION | | | | | | |
|---|---|---|---|---|---|---|---|
| | $CH_3Cl$ | $CH_2Cl_2$ | $CHCl_3$ | $CCl_4$ | CO | $CO_2$ | HCOOH |
| Cu | 30.03 | 39.42 | 9.39 | 0.14 | 0.00 | 12.44 | 8.58 |
| Co | 44.31 | 12.44 | 1.32 | 0.00 | 0.00 | 3.67 | 38.26 |
| Ni | 23.0 | 3.78 | 0.00 | 0.00 | 0.00 | 0.00 | 73.19 |
| Pb | 20.97 | 3.49 | 0.37 | 0.00 | 0.00 | 0.00 | 75.17 |
| Ag | 12.71 | 1.37 | 0.09 | 0.00 | 0.00 | 14.52 | 71.31 |
| Pt[a] | 31.26 | 3.49 | 0.30 | 0.18 | 0.00 | 17.35 | 47.42 |
| Pt[b] | 28.96 | 3.28 | 0.42 | 0.14 | 0.00 | 10.75 | 56.45 |
| Cr | 10.92 | 2.66 | 0.60 | 0.00 | 64.77 | 21.05 | 0.00 |
| BLANK | 10.10 | 0.45 | 0.09 | 0.00 | 69.55 | 7.02 | 12.78 |

[a] After 24 hours.
[b] After 48 hours.

As stated above, it is of advantage to minimize the polychloromethane production in order to protect the catalysts. It is also of note that limiting the polychloromethane production also limits water production that must be removed in recovering the formic acid product.

It is therefore seen that the present invention provides an improved method for the production of monochloromethane and other chlorinated alkanes from methane. The methane can be provided from natural gas supplies or from that which ordinarily is removed in a coal gasification process. Through use of one of the selected oxyhydrochlorination catalysts in accordance with the invention increased selectively of monochloromethane over polychloromethanes is achieved along with the production of economically recoverable quantities of formic acid. Using a straight forward condensation separation, formic acid concentrations of 20–30% and higher can be obtained for subsequent further concentration by fractionation or azeotropic distillation. Improved conversions of the methane are achieved through use of the cobaltous chloride catalyst to enhance productivity in a second reaction over zeolite for the production of gasoline boiling fractions with recycle of release HCl.

Although the invention is described in terms of specific embodiments and process parameters, it will be clear to one skilled in the art that various modifications in the procedures and materials can be made within the scope of the following claims.

The embodiment of the invention in which an exclusive property or privilege is claimed is defined as follows:

1. A catalytic method for the production of monochloromethane with recoverable concentrations of formic acid in aqueous solution but with limited polychloromethane production comprising:
   providing an oxyhydrochlorination catalyst including a pyrogenic support material, a first layer of catalyst including a metal chloride deposited on the support material, said metal chloride selected from the group consisting of chlorides of cobalt, lead, silver and nickel, and a second layer of catalyst including an alkali metal chloride and permissibly a rare earth chloride deposited on the support;
   contacting the catalyst with a reactant gas mixture containing methane, HCl and oxygen at reaction conditions to produce a normalized carbon-product distribution of at least 20 mole % formic acid and monochloromethane in excess of the total polychloromethane production.

2. The method of claim 1 wherein the formic acid is separated from other carbon products by condensation in a formic acid-water solution and then concentrated to about 75% to 90% formic acid as a product of the process.

3. The method of claim 2 wherein the solution of formic acid and water is concentrated by distillation to a constant boiling composition of formic acid and water.

4. The method of claim 2 wherein the catalyst deposited in the first layer includes a metal chloride selected from the group consisting of chlorides of cobalt, lead and nickel.

5. The method of claim 1 wherein the catalyst deposited in the first layer includes cobaltous chloride in combination with a second layer including potassium chloride and lanthanum chloride.

6. The method of claim 1 wherein the catalyst includes $PbCl_2$ and the gaseous mixture is passed into contact with the catalyst at a temperature of about 350° to 450° C. to produce a mixture of formic acid, chlorinated alkanes and water.

7. The method of claim 1 wherein the gas mixture is passed into contact with the catalyst at a temperature of about 300° C. to 400° C. for a residence time of about 7 to 10 seconds.

8. The method of claim 1 wherein the gas mixture is passed into contact with the catalyst at a temperature of about 340° C. for a residence time of about eight seconds.

9. The method of claim 1 wherein the monochloromethane is separated from the aqueous formic acid and dried followed by reaction over a crystalline aluminosilicate catalyst to produce hydrocarbons in the C-5 to C-10 range and HCl, said HCl is recycled to the oxyhydrochlorination catalyst for reaction with additional methane.

10. The method of claim 1 wherein the reactant gas mixture includes about equal flows of methane and HCl and an oxygen flow of about one half that of methane.

* * * * *